Figure 1:
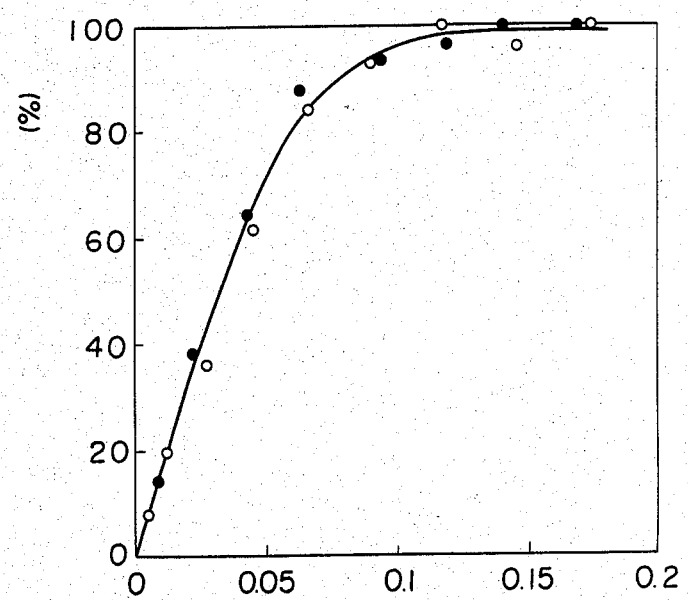

United States Patent [19]

Komatsu et al.

[11] Patent Number: 4,530,745

[45] Date of Patent: Jul. 23, 1985

[54] METHOD FOR ELECTROLYZING CEROUS SULFATE

[75] Inventors: Tatsuyoshi Komatsu, Kamakura; Shigeaki Numata; Katsuhiko Hioki, both of Yokohama; Toshihiko Sumino, Kawasaki, all of Japan

[73] Assignee: Kawasaki Kasei Chemicals Ltd., Tokyo, Japan

[21] Appl. No.: 620,095

[22] Filed: Jun. 13, 1984

[30] Foreign Application Priority Data

Jul. 5, 1983 [JP] Japan .................................. 58-121790

[51] Int. Cl.³ .............................................. C25B 1/00
[52] U.S. Cl. ................................................... 204/130
[58] Field of Search ........................................ 204/130

[56] References Cited

U.S. PATENT DOCUMENTS 4,312,721  1/1982  Oehr ...................................... 204/78

Primary Examiner—R. L. Andrews

Attorney, Agent, or Firm—Oblon, Fisher, Spivak, McClelland & Maier

[57] ABSTRACT

A method for electrolyzing cerous sulfate in the electrolytic oxidation of cerous sulfate to ceric sulfate in an aqueous sulfuric acid solution, characterized in that the concentration of the cerous sulfate in the electrolyte to be supplied to the electrolytic cell is maintained, by the presence of ceric sulfate, at a level of at least the saturated concentration of cerous sulfate in the aqueous sulfuric acid solution (exclusive of the cerous sulfate and ceric sulfate) at the initial sulfuric acid concentration and at the temperature of electrolysis, and at most the saturated concentration of cerous sulfate in the presence of the ceric sulfate in the aqueous sulfuric acid solution at the initial sulfuric acid concentration and at the temperature of electrolysis, and the concentration of the ceric sulfate in the electrolyte is maintained at a level of at most the saturated concentration of ceric sulfate in the aqueous sulfuric acid solution at the initial sulfuric acid concentration and at the temperature of electrolysis.

4 Claims, 5 Drawing Figures

METHOD FOR ELECTROLYZING CEROUS SULFATE

The present invention relates to a method for electrolytically oxidizing cerous sulfate dissolved in an aqueous sulfuric acid solution to ceric sulfate in an industrially advantageous manner. More particularly, it relates to a method for electrolytically oxidizing cerous sulfate formed by the oxidation of an oxidizable compound with ceric sulfate dissolved in an aqueous sulfuric acid solution, to regenerate ceric sulfate in an industrially advantageous manner.

Heretofore, it has been known to oxidize an organic compound such as naphthalene by means of a ceric sulfate-aqueous sulfuric acid solution to obtain an oxidation product corresponding to the organic compound, such as 1,4-naphthoquinone (Japanese Examined Patent Publication No. 34978/1974 and Japanese Unexamined Patent Publication No. 61321/1981). By the oxidation reaction with ceric sulfate, the ceric sulfate is reduced to cerous sulfate. As the cerium compound is expensive, it is common to employ a method for oxidizing cerous sulfate formed by the reduction to regenerate ceric sulfate, which is then recycled for reuse in the above-mentioned oxidation reaction. As a method for regenerating ceric sulfate from cerous sulfate, there have been proposed an electrochemical method such as an electrolytic method, or a chemcial method for oxidation and regeneration. However, it is common to employ a method wherein cerous sulfate is oxidized by electrolysis for regeneration.

As a method for electrolyzing a cerous sulfate-aqueous sulfuric acid solution, there may be mentioned, for instance, a method wherein a cerous sulfate-aqueous sulfuric acid solution formed by the reduction of the ceric sulfate as a result of the oxidation reaction of an oxidizable compound with ceric sulfate, is electrolytically oxidized in a batch system or in a continuous system by using a diaphragm such as an ion exchange membrane and an electrode made of e.g. lead dioxide-coated titanium, platinum-electroplated titanium, iridium-titanium or platinum-iridium-titanium as an anode, to regenerate a ceric sulfate-aqueous sulfuric acid solution, as disclosed in e.g. Japanese Examined Patent Publication No. 34978/1974, Japanese Unexamined Patent Publication No. 61321/1981, Toshi Ishino et al., Technol. Rept. Osaka Univ. 10, pages 261–269 (1960), Japanese Examined Patent Publication No. 41561/1970 and U.S. Pat. No. 4,312,721. However, in each of these conventional methods, the concentration of cerous sulfate in the electrolyte to be supplied to the electrolytic cell used to be at most about 0.1 mol/liter (about 0.2 mol/liter as the concentration of cerium (ions) contained in the molecule of cerous sulfate). In other words, the electrolysis was conducted at a cerous sulfate concentration of at most the maximum solubility of cerous sulfate in an aqueous sulfuric acid solution at the sulfuric acid concentration and the temperature at the time of the electrolysis. Namely, the maximum solubility or the saturated concentration of cerous sulfate in the aqueous sulfuric acid solution is determined by the concentration of the sulfuric acid and the temperature. For instance, it is 0.125 mol/liter in a 6% sulfuric acid aqueous solution at 50° C.; 0.115 mol/liter and 0.05 mol/liter in 10% sulfuric acid aqueous solutions at 50° C. and 80° C., respectively; and 0.11 mol/liter and 0.05 mol/liter in 14% sulfuric acid aqueous solutions at 50° C. and 80° C., respectively. Thus, the saturated concentration of cerous sulfate is substantially lower than the saturated concentration of ceric sulfate, which is (e.g. 0.67 mol/liter in a 6% sulfuric acid aqueous solution at 50° C.). It used to be believed that the electrolysis has to be conducted at a concentration of not higher than the saturated concentration of cerous sulfate. In such conventional electrolysis of cerous sulfate, the concentration of cerous sulfate easily drops below 0.1 mol/liter by the electrolysis, whereby it is impossible to improve the current efficiency. Besides, the concentration of ceric sulfate obtained by such electrolysis and intended to be used for the oxidation reaction of an oxidizable compound, is limited to a level substantially lower than the saturated concentration of ceric sulfate, whereby the amount of the solution, per product, to be used for the electrolysis and reaction increases and the heat loss becomes great. Consequently, there will be industrial difficulties such that the current efficiency, the installation efficiency and the heat efficiency decrease to a large extent. Thus, it used to be believed that the industrial application of such electrolysis was difficult.

The present inventors have conducted extensive researches with an aim to solve the above-mentioned industrial difficulties of the conventional method and to provide an industrially advantageous method for electrolysis by using a cerous sulfate-aqueous sulfuric acid solution. As a result of experiments conducted by the present inventors, it has been found firstly that for the improvement of the current efficiency in the electrolytic oxidation of a cerous sulfate-aqueous sulfuric acid solution, not only the agitation of the electrolyte in the electrolytic cell or the linear velocity of the flow of the electrolyte, the temperature of electrolysis and the current density, but also the concentration of cerous sulfate in the electrolyte, i.e. the aqueous sulfuric acid solution, is extremely influential. For instance, as shown in FIG. 1, the current efficiency sharply drops when the cerous sulfate concentration in the aqueous sulfuric acid solution is low, especially as low as less than 0.1 mol per liter, even under favourable conditions for obtaining high current efficiency by means of a forced-flow diaphragm electrolytic cell. As a result of further researches, the present inventors have found that while the solubility of ceric sulfate in the aqueous sulfuric acid does not substantially change by the coexistence of cerous sulfate, the solubility of cerous sulfate in an aqueous sulfuric acid solution remarkably increases as the amount of the co-existing ceric sulfate increases. Accordingly the concentration of cerous sulfate in the aqueous sulfuric acid solution for the electrolysis, can be substantially increased over the case of the above-mentioned conventional electrolysis, by the presence of ceric sulfate. The current efficiency in the electrolytic oxidation of such a cerous sulfate-ceric sulfate-aqueous sulfuric acid solution, shows the same relation with the concentration of cerous sulfate as the current efficiency in the case of the electrolytic oxidation of the cerous sulfate-aqueous sulfuric acid solution as shown in FIG. 1 even when ceric sulfate is present. The present invention is based on these discoveries.

Namely, the present invention provides a method for electrolyzing cerous sulfate in the electrolytic oxidation of cerous sulfate to ceric sulfate in an aqueous sulfuric acid solution, characterized in that the concentration of the cerous sulfate in the electrolyte to be supplied to the electrolytic cell is maintained, by the presence of ceric sulfate, at a level of at least the saturated concentration of cerous sulfate in the aqueous sulfuric acid solution (exclusive of the cerous sulfate and ceric sulfate) at the initial sulfuric acid concentration and at the temperature of electrolysis, and at most the saturated concentration of cerous sulfate in the presence of the ceric sulfate in the aqueous sulfuric acid solution at the initial sulfuric acid concentration and at the temperature of electrolysis, and the concentration of the ceric sulfate in the electrolyte is maintained at a level of at most the saturated concentration of ceric sulfate in the aqueous sulfuric acid solution at the initial sulfuric acid concentration and at the temperature of electrolysis.

Now, the present invention will be described with reference to the preferred embodiments.

In the accompanying drawings,

FIG. 1 is a graph showing the relation of the current efficiency with the concentration of cerous sulfate in a cerous sulfateceric sulfate-aqueous sulfuric acid solution system. The electrolysis was conducted at a current density of 16.3 A/dm$^2$, with an aqueous sulfuric acid concentration of 10%, at an electrolytic temperature of 50° C. and at a linear velocity of the electrolyte of 0.4 m/sec by using a diaphragm made of a fluorinated resin-type cation exchange membrane, with the cathode being a net-type SUS 316L electrode and the anode being a net-type platinum/titanium electrode (symbol mark ○ in the Figure) or a platinum-iridium/titanium electrode (symbol mark ● in the Figure).

Figure 2:
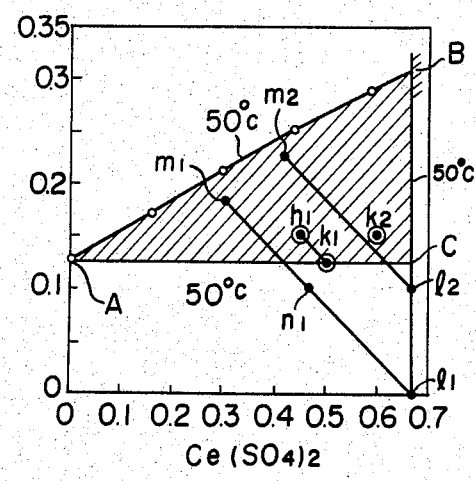
Figure 3:
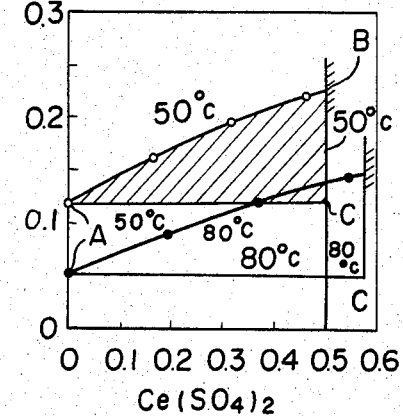
Figure 4:
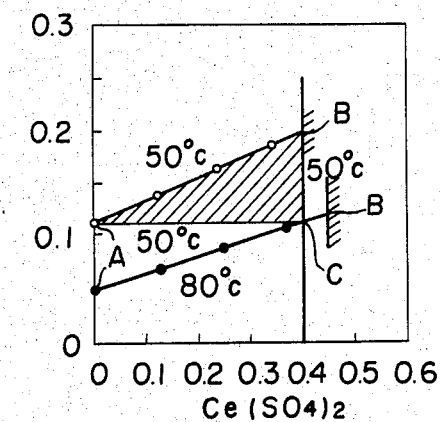

FIGS. 2 to 4 are graphs illustrating the solubility of cerous sulfate relative to the concentration of the coexisting ceric sulfate in an aqueous sulfuric acid solution. FIG. 2 illustrates the solubility in a 6% sulfuric acid aqueous solution, FIG. 3 illustrates the solubility in a 10% sulfuric acid aqueous solution and FIG. 4 illustrates the solubility in a 14% sulfuric acid aqueous solution, respectively at 50° C. or 80° C. In the Figures, symbol A represents the saturated concentration of cerous sulfate, and symbol B represents the saturated concentration of ceric sulfate.

Figure 5:
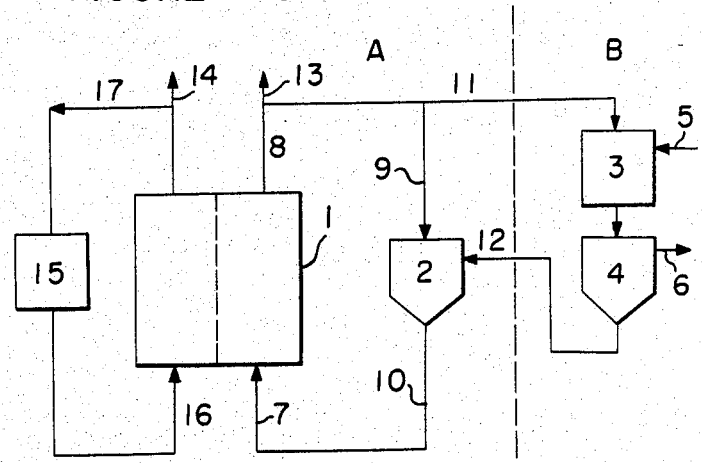

FIG. 5 is a simplified flow sheet of a recycling process for conducting the electrolysis of the present invention in a continuous manner, wherein the electrolysis system (A side) is combined with the reaction system (B side) for oxidizing an oxidizable compound (for instance, an organic compound such as naphthalene).

As the oxidizable compound to be oxidized by ceric sulfate dissolved in the ceric sulfate-cerous sulfate-aqueous sulfuric acid solution regenerated by the electrolytic oxidation of cerous sulfate by the method of the present invention, there may be mentioned an organic compound. Specifically, there may be mentioned unsubstituted or substituted compounds of polynuclear aromatic hydrocarbons such as naphthalene, anthracene, diphenyl, pyrene, phenanthrene, nitronaphthalene, 2-methylnaphthalene, 2-tert-butylnaphthalene, 2-chloronaphthalene, tetralin or 2-ethylanthracene; toluene and its derivatives such as, xylene, p-nitrotoluene, p-methoxytoluene or p-phenoxytoluene; and a secondary alcohol such as 4-dodecanol. When oxidized by ceric sulfate, they produce the corresponding quinones, aldehydes or ketones. As specific examples of the products, there may be mentioned 1,4-naphthoquinone, anthraquinone, 2-phenylbenzoquinone, pyrenequinone, 9,10-phenanthraquinone, 5-nitro-1,4-naphthoquinone, 2-methyl-1,4-naphthoquinone, 2-tert-butyl-1,4-naphthoquinone, 2-chloro-1,4-naphthoquinone, tetralone or 2-ethylanthraquinone; benzaldehyde, tolualdehyde, p-nitrobenzaldehyde, anisaldehyde, p-phenoxybenzaldehyde and their derivatives; and a ketone such as 4-dodecanone.

The oxidation reaction of the oxidizable compound (the organic compound) with ceric sulfate dissolved in the above-mentioned ceric sulfate-cerous sulfate-aqueous sulfuric acid solution, is usually conducted in the following manner. Namely, the oxidizable compound (the organic compound) and the ceric sulfate-cerous sulfate-aqueous sulfuric acid solution having a predetermined composition, are reacted, under stirring, at a temperature of from 40° to 80° C. in the presence or absence of an organic solvent immiscible with water and, if necessary, in the presence of a dispersant. This oxidation reaction is preferably conducted under such condition that whole cerous sulfate inclusive of cerous sulfate formed by the reaction, is in a dissolved state (for instance, in the state shown by the inside or dissolved side of "the solubility curves of cerous sulfate relative to the concentration of ceric sulfate in the aqueous sulfuric acid solution" in FIGS. 2 to 4.).

After the oxidiation reaction, the reaction product is separated by means of a conventional separation means such as precipitation, filtration or liquid-liquid separation by extracting it into an organic solvent immiscible with water, and if necessary, the reaction product in the aqueous layer after the separation is further extracted with a solvent. The reaction product may be obtained in a solid form as it is or after removing the solvent. Alternatively, the product may be used as a starting material for the next reaction, in the state as dissolved in the above-mentioned organic solvent or if necessary, after purification.

As the water-immiscible organic solvent to be used in the above oxidation reaction, there may be mentioned an aromatic hydrocarbon or its derivatives, such as tert-butylbenzene or chlorobenzene; an aliphatic hydrocarbon such as n-hexane, n-pentane or n-octane; or a chlorinated aliphatic hydrocarbon such as carbontetrachloride, chloromethylene, difluoroethane, trichloroethane or tetrachloroethane. These organic solvents are non-reactive with ceric sulfate.

Thus, the aqueous layer after the separation of product formed by the oxidation reaction of the oxidizable compound (the organic compound) with ceric sulfate, contains cerous sulfate and ceric sulfate. When such an aqueous layer is supplied to the electrolytic cell to conduct the electrolysis of cerous sulfate according to the present invention, it is preferred that the aqueous layer is in the state of a solution in order to avoid deposition of crystals of e.g. cerous sulfate on the electrolytic cell or the electrodes, diaphragms or spacers of the electrolytic cell, or to prevent the abrasion of such materials by the crystals.

In the electrolysis of cerous sulfate of the present invention, hydrogen is formed at the cathode, and ceric ions as major products and oxygen as a by-product are formed at the anode, as shown by the following formulas:

Cathode: 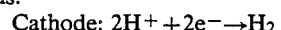$2H^+ + 2e^- \rightarrow H_2$

Anode: 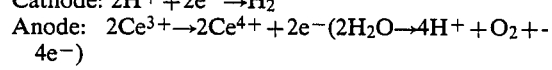$2Ce^{3+} \rightarrow 2Ce^{4+} + 2e^- (2H_2O \rightarrow 4H^+ + O_2 + 4e^-)$ As a method for electrolyzing an aqueous solution of this type, it is usually preferred to employ a forced circulation type continuous electrolytic system as shown on the A side of the flow sheet in FIG. 5. Namely, at the cathode side, a catholyte circulation system is provided which comprises a catholyte tank 15 connected by conduits 16 and 17 to a diaphragm-type electrolytic cell 1 and a discharge pipe 14 for the generated gas. On the other hand, at the anode side, a continuous circulation electrolytic system for forcibly circulating the electrolyte is provided which comprises an anolyte preparation tank 2 connected by conduits 7, 8, 9 and 10 to the electrolytic cell 1 and a discharge pipe 13 for the generated gas. A part of the electrolyte from the elecrolytic cell 1 in such a continuous circulation electrolytic system, is fed through a conduit 11 to a reactor 3 in the system for the oxidation reaction of an organic compound with ceric sulfate, as shown on the B side of the flow sheet in FIG. 5, and used for the oxidation reaction of the oxidizable feed material (the organic compound) supplied to the reactor 3 from a supply pipe 5, in the presence or absence of an organic solvent. After the oxidation reaction, the oxidation reaction product of the above oxidizable feed material (the organic compound) is separated in a separator 4 in the presence or absence of an organic solvent, withdrawn through a dishcarge pipe 6 and then supplied for the product process. On the other hand, the aqueous layer after the separation of the oxidation reaction product of the oxidizable feed material (the organic compound), is withdrawn from the separator 4 through a discharge pipe 12 and introduced into the above-mentioned preparation tank 2, and after being adjusted to have a predetermined electrolyte composition, it is supplied to the electrolytic cell 1 via a discharge pipe 10 and a supply pipe 7 for the electrolytic cell. Thus, the continuous circulation process comprising the A and B sides, as illustrated as an embodiment in the flow sheet in FIG. 5, can be employed industrially most advantageously. However, if necessary, a batch system or a non-circulation system as shown in e.g. Japanese Examined Patent Publication No. 34978/1974, may also be employed.

As the diaphragm-type electrolytic cell 1, it is common to employ the one having a structure commonly employed for the electrolysis of an aqueous electrolyte solution. For instance, as disclosed in Japanese Examined Patent Publication No. 41561/1970, the electrodes may be made of materials which are chemically resistant under the condition in which they are used. In the case of a cathode, it is usual to employ a material which has a sufficiently low hydrogen overvoltage to discharge hydrogen prior to the reduction of the metal ions to a zero-valence state. Whereas, in the case of an anode, it is usual to employ a material which has a sufficiently high oxygen overvoltage to oxidize cerous ions by active oxygen generated competitively with the discharge of the oxygen or accidentally at the anode interface under the electrolytic condition and chemically adsorbed, or by an assistance of a sufficiently strong chemical oxidizing agent such as lead dioxide. Therefore, as a suitable anode material, there may be employed an electrode coated with platinum or a platinum-group metal alloy, such as platinum, platinum-plated titanium, iridium/titanium or platinum-iridium/titanium, or lead dioxide-lead coated titanium, magnetite or ferrite. As a cathode material, there may be employed platinum, titanium, zirconium, tantalum, stainless steel or graphite. As a shape of the electrode, it is common to employ a flat plate or a metal net type. Further, as a diaphragm, there may be mentioned a neutral diaphragm, a cation exchange membrane or an anion exchange membrane. Specifically, as the neutral diaphragms, there may be mentioned finely porous diaphragms made of e.g. finely fibrous glass matt, polypropylene or poly(tetrafluoroethylene). As the ion exchange membranes, there may be mentioned Nafion (manufactured by DuPont Co.), Selemion (Asahi Glass Co., Ltd.) or Aciplex (Asahi Chemical Industries Co., Ltd.). However, it is preferred to employ a fluorinated resin-type cation exchange membrane or a fluorinated resin-type neutral membrane.

As an electrolytic cell to be used for the electrolysis of the present invention, it is advantageous to employ a cell provided with a diaphragm with a view to preventing the mixing of the generated gaseous oxygen and gaseous hydrogen, preventing the migration of the ceric ions formed by the oxidation at the anode, from the anode to the cathode, and selectively permitting hydrogen ions to pass therethrough to improve the current efficiency. However, it is possible to employ a diaphragm-less cell so long as it has a structure whereby oxygen and hydrogen generated from both electrodes, can adequately and safely be separated. Further, it is common to employ a forced circulation system for the electrolytic cell, and to employ a system wherein unit electrolytic cells are arranged in parallel or in series or in a combination of both types. Further, the electrolytic cell may be of a unipolar type or a bipolar type. In a diaphragm-type electrolytic cell to be used for the electrolytic oxidation of cerous sulfate, it is common to supply an electrolyte containing cerous ions to the anode side and dilute sulfuric acid to the cathode side.

When the electrolytic oxidation of cerous sulfate is conducted on an industrial scale, it is necessary to maintain cerous sulfate in the electrolyte to be supplied to the electrolytic cell at a concentration of not higher than its solubility in order to avoid clogging of the electrolytic cell due to the precipitation (i.e. deposition) or sedimentation of crystals in the cell. At the same time, as is evident also from FIG. 1, it is necessary to maintain the concentration of cerous sulfate in the electrolyte at a level of at least 0.08 mol/liter, preferably at least 0.1 mol/liter in order to improve the current efficiency, energy efficiency and installation efficiency.

However, in order to satisfy the necessary conditions by the conventional method, the concentration of cerous sulfate in the electrolyte has to be at most the saturated concentration of cerous sulfate (i.e. the maximum solubility of cerous sulfate, e.g. 0.125 mol/liter in the 6% sulfuric acid aqueous solution at 50° C. in FIG. 2, 0.115 mol/liter in the 10% sulfuric acid aqueous solution at 50° C. in FIG. 3, or 0.11 mol/liter in the 14% sulfuric acid aqueous solution at 50° C. in FIG. 4) as shown by point A at the left-hand side of each of FIGS. 2 to 4. In order to obtain high current efficiency at the same time, it will be necessary to maintain a high linear velocity of the flow of the electrolyte and/or a low current density, or to conduct the electrolysis in an extremely narrow operational range of the cerous sulfate concentration, thus leading to practical difficulties from the industrial point of view.

Whereas, according to the method of the present invention for the electrolysis of cerous sulfate, ceric sulfate is initially present in the electrolyte to be supplied to the electrolytic cell, whereby (1) the concentration of cerous sulfate in the electrolyte can be maintained at a level of at least the saturated concentration of cerous sulfate in an aqueous sulfuric acid solution at the initial sulfuric acid concentration and at the temperature of electrolysis, and (2) at most the saturated concentration of cerous sulfate relative to the concentration of ceric sulfate which is coexistent in the aqueous sulfuric acid solution at the initial concentration and at the temperature of electrolysis, and (3) the concentration of the ceric sulfate is adjusted to be maintained at a level of at most the saturated concentration of ceric sulfate in the aqueous sulfuric acid solution at the initial concentration and the temperature of electrolysis, thus adequately satisfying the requirements for the above-mentioned industrial application and solving the industrial difficulties of the conventional method.

Now, the above-mentioned requirements (1), (2) and (3) for the electrolysis of the present invention, i.e. the ranges of the concentrations of cerous sulfate and ceric sulfate in the electrolyte to be supplied to the electrolytic cell, will be specifically described with reference to FIGS. 2, 3 and 4. For instance, in the case of an electrolyte to be supplied to the electrolytic cell at 50° C., the required concentrations fall within the hatched range defined by three lines i.e. a curve AB and straight lines AC and BC in each Figure (hereinafter referred to simply as a "ABC hatched portion"). Namely, the curve AB in FIG. 2 is a curve of the solubility (the saturated molar concentration) of cerous sulfate $[Ce_2(SO_4)_3]$ relative to the molar concentration (abscissa) of ceric sulfate $[Ce(SO_4)_2]$ which is coexistent in the 6% sulfuric acid aqueous solution at 50° C., and thus indicates the upper limit of the molar concentration of cerous sulfate relative to the molar concentration of ceric sulfate coexistent in the aqueous sulfuric acid solution as specified in the above requirement (2). The straight line AC in FIG. 2 is a straight line parallel with the abscissa, and thus indicates a predetermined value corresponding to the lower limit of the molar concentration of cerous sulfate as specified in the above requirement (1) i.e. the saturated concentration (0.125 mol/liter) of cerous sulfate in the aqueous sulfuric acid solution. Further, the straight line BC in FIG. 2 is a straight line parallel with the ordinate, and thus indicates a predetermined value corresponding to the upper limit of the molar concentration of ceric sulfate as specified in the above requirement (3) i.e. the saturated concentration (0.67 mol/liter) of ceric sulfate in the aqueous sulfuric acid solution. The meaning of the hatched portion (i.e. the ABC hatched portion) defined by such three lines i.e. the curve AB and straight lines AC and BC, is likewise applicable to the case of the 10% sulfuric acid aqueous solution at 50° C. in FIG. 3 and to the case of the 14% sulfuric acid aqueous solution at 50° C. in FIG. 4. Further, in the case of an electrolyte to be supplied to the electrolytic cell at 80° C., the concentrations of cerous sulfate and ceric sulfate should likewise be within the range defined by the curve AB at 80° C. and straight lines AC and BC at 80° C. in the case of the 10% sulfuric acid aqueous solution at 80° C. as shown at the lower part of FIG. 3.

According to the electrolysis of the present invention, once the concentrations of cerous sulfate and ceric sulfate in the electrolyte are adjusted to satisfy the above-mentioned requirements of the present invention, e.g. adjusted to be within the ABC hatched portion in FIG. 2, at the inlet before being supplied to the electrolytic cell 1 via a supply pipe 7 as shown in the flow sheet in FIG. 5, the composition of the electrolyte at the outlet of the electrolytic cell 1 i.e. the composition of the electrolyte flowing out via a discharge pipe 8, may take any optional concentration outside the ABC hatched portion in FIG. 2 since the electrolyte can be maintained in the form of a solution so long as the concentration does not exceeds the solubility of the ceric sulfate. Thus, the electrolysis of the present invention is particularly advantageous when employed for the case where the differences between the concentrations of the cerous sulfate and ceric sulfate as between the inlet and the outlet are substantial, for instance, in an operation to improve the conversion of cerous ions to ceric ions (e.g. in a case of a low flow rate or a serial arrangement). For instance, in FIG. 2, when an electrolyte having a composition represented by $m_1[Ce_2(SO_4)_3=0.18$ mol/liter and $Ce(SO_4)_2=0.3$ mol/liter] or $m_2[Ce_2(SO_4)_3=0.225$ mol/liter and $Ce(SO_4)_2=0.42$ mol/liter] at the inlet of the electrolytic cell, is supplied to the electrolytic cell, the concentration of the cerous sulfate gradually decreases and the concentration of ceric sulfate gradually increases as the electrolysis proceeds. The operation lines indicating the changes of the concentration in such cases, are shown by a straight line $m_1l_1$ and a straight line $m_2l_2$ (each of $l_1$ and $l_2$ represents the saturated concentration of ceric sulfate). It should be understood from such operation lines that according to the electrolysis of the present invention shown at the A side in FIG. 5, it is possible to adopt greater changes in the concentrations than the conventional method, and accordingly not only the current efficiency can be improved in the electrolysis of the present invention, but also it is possible to reduce the amount of the solution to be used for the oxidation reaction of the oxidizable compound (i.e. the organic compound) at the B side in FIG. 5, whereby the entire process in FIG. 5 can be conducted in an industrially advantageous manner.

If it is intended to obtain current efficiency as high as possible, the electrolyte composition at the outlet of the electrolytic cell may be maintained at e.g. $n_1$ in FIG. 2 where the concentration of cerous sulfate is 0.1 mol/liter or higher. On the other hand, when a forced circulation system is employed wherein electrolytic cells are arranged in parallel with one another to increase the amount of the circulation of the electrolyte i.e. the linear velocity, the change in the composition of the electrolyte as between the inlet and the outlet of the electrolytic cell, is minimized, and accordingly it is possible to conduct the electrolysis at a high current efficiency and with a high concentration of cerous sulfate by adjusting the inlet composition to be $h_1[Ce_2(SO_4)_3=0.15$ mol/liter and $Ce(SO_4)_2=0.45$ mol/liter] and the outlet composition to be $k_1[Ce_2(SO_4)_3=0.125$ mol/liter and $Ce(SO_4)_2=0.50$ mol/liter], or by adopting $k_2[Ce_2(SO_4)_3=0.15$ mol/liter and $Ce(SO_4)_2=0.60$ mol/liter] where no substantial change is observed as between the inlet and the outlet of the electrolytic cell, in FIG. 2. In such a case, the change in the composition of the electrolyte as between the inlet and the outlet of the electrolytic cell, is maintained in an equilibrium state by the balance between the amount of the withdrawal (via the conduit 11) to the reaction system at the B side in FIG. 5 and the amount recycled (via the conduit 12) to the electrolysis system at the A side in FIG. 5 from the reaction system, as mentioned above with respect to FIG. 5.

As discussed in the foregoing, when the entire process of FIG. 5 is taken into account including the materials, current efficiency and energy efficiency in the electrolysis system of cerous sulfate at the A side in FIG. 5 as well as the operational conditions in the oxidation reaction system of the oxidizable compound (i.e. the organic compound) with ceric sulfate at the B side in FIG. 5, a preferred embodiment of the method of the present invention for the electrolysis of cerous sulfate, which is capable of providing a distinct industrial effectiveness over the conventional method, may be summarized as follows.

Electrolytic temperature:
  30°–80° C., preferably 40°–80° C., more preferably 40°–60° C.

Current density:
  5–30 A/dm$^2$, preferably 10–20 A/dm$^2$

Electrolyte composition at the inlet of the electrolytic cell:
  (a) Sulfuric acid concentration: about 5–about 15%, preferably about 6–about 12%, more preferably about 6–about 10%
  (b) Cerous sulfate concentration: at least 0.08 mol/liter, preferably at least 0.1 mol/liter, more preferably at least 0.12 mol/liter, and at most 0.30 mol/liter, preferably at most 0.20 mol/liter, more preferably at most 0.18 mol/liter
  (c) Ceric sulfate concentration: at most the saturated concentration, and at least 0.28 mol/liter, more preferably at least 0.30 mol/liter Electrolyte composition at the outlet of the electrolytic cell:
  (a) Sulfuric acid concentration: same as the above (a)
  (b) Cerous sulfate concentration: at least 0.06 mol/liter, preferably at least 0.08 mol/liter, more preferably at least 0.1 mol/liter
  (c) Ceric sulfate concentration: at most the saturated concentration, preferably at most 0.6 mol/liter and at least 0.35 mol/liter Water will be consumed by the electrolytic reaction. Therefore, water is supplemented at a proper portion of the electrolysis system, for instance, at the anolyte preparation tank 2 in FIG. 5.

Now, the present invention will be described in further detail with reference to Examples. In this specification, "%" means "% by weight" unless otherwise specified.

EXAMPLE 1: (Semi-continuous batch system electrolysis)

(1) Into an anolyte preparation tank, 1.16 kg of ceric sulfate, 0.98 kg of cerous sulfate and 10.6 kg of a 8% sulfuric acid aqueous solution were taken to obtain an anolyte having a total volume of about 10 liters. The concentrations of the ceric sulfate and cerous sulfate in the anolyte were 0.349 mol/liter and 0.173 mol/liter, respectively. On the other hand, into a catholyte tank, about 10 liters of a 8% sulfuric acid aqueous solution was fed as a catholyte.

In the electrolytic cell, a metal net-type platinum electroplated titanium plate was used as an anode, a metal net-type stainless steel (SUS 316L) plate was used as a cathode, and a fluorinated resin-type cation exchange membrane was used as a diaphragm. To the anode and the cathode of this electrolytic cell, the anolyte and catholyte were supplied from the anolyte preparation tank and the catholyte tank, respectively. The electrolysis was conducted at an electrolytic temperature of 50° C., at a voltage of from 2.8 to 3.2 V at a current density of 16.34 A/dm$^2$ and at the linear velocity of the flow of the electrolyte in the electrolytic cell of 0.4 m/sec. The anolyte and the catholyte discharged from the electrolytic cell, were returned to the above-mentioned anolyte preparation tank and the catholyte tank, respectively, and again recycled to the electrolytic cell. Thus, the concentration of cerous ions in the anolyte preparation tank decreased as time passed, and the concentration of ceric ions increased inversely.

About 2 hours later, the concentration of cerous sulfate in the anolyte in the anolyte preparation tank reached 0.120 mol/liter, and the electrolysis was terminated. The concentration of ceric sulfate at that time was 0.455 mol/liter. The current efficiency was 98.5%.

(2) Then, by using the electrolyte obtained in the above (1), an experiment for the oxidation of naphthalene was conducted.

Into a glass-lined reactor equipped with a stirrer and a buffle, the electrolyte and a solution prepared by dissolving 340 g (2.66 mols) of naphthalene in 350 g of tert-butylbenzene, were fed and reacted at 50° C. under forcible stirring. When the ceric sulfate concentration in the aqueous layer reached about 0.35 mol/liter (cerous sulfate concentration: 0.17 mol/liter), the reaction was terminated.

After the reaction, the oil layer and the aqueous layer were separated. Naphthoquinone dissolved in the aqueous layer was extracted twice with 3 liters of tertbutyl-benzene, and the extraction oil layer (tert-butylbenzene layer) thereby obtained was combined with the above-mentioned oil layer separated after the reaction. The combined oil layer was subjected to a high speed liquid chromatography, whereby naphthoquinone and unreacted naphthalene were analyzed. As the results, the amount of naphthoquinone and the amount of recovered naphthalene were 23.9 g and 320 g, respectively. Thus, the yield of naphthoquinone per reacted naphthalene was 97 molar %.

On the other hand, the concentration of ceric sulfate in the aqueous layer was 0.35 mol/liter, and the concentration of cerous sulfate was 0.171 mol/liter.

(3) By using the aqueous layer after the extraction of naphthoquinone, the electrolysis and oxidation reaction were conducted in the same manner as in the above (1) and (2), whereby similar results were obtained.

EXAMPLE 2: (Platinum-iridium/titanium electrode was used)

The experiment was conducted in the same manner as in Example 1 except that instead of the platinum-electroplated titanium electrode, a platinum-iridium-sintered titanium electrode was used as the anode.

The results thereby obtained were the same as those of Example 1 except that the current efficiency at a voltage of from 2.5 to 3.1 V was 99.0%.

EXAMPLE 3: (Graphite plate electrode was used)

The experiment was conducted in the same manner as in Example 1 except that instead of the stainless steel (SUS 316L) electrode, a graphite plate electrode was used as the cathode.

The results thereby obtained were the same as those of Example 1 except that the current efficiency at a voltage of from 2.8 to 3.4 V was 96%.

EXAMPLE 4: (Neutral membrane was used as the diaphragm)

The experiment was conducted in the same manner as in Example 1 except that instead of the cation exchange membrane, a fluorinated resin-type porous diaphragm was used as the diaphragm.

The results thereby obtained were the same as those of Example 1 except that the current efficiency at a voltage of from 2.73 to 3.13 V was 96.0%.

EXAMPLE 5: (Forced circulation-type continuous electrolysis)

In a continuous electrolysis system as shown at the A side of the flow sheet of the circulation process in FIG. 5, the electrolysis of cerous sulfate was conducted under the following conditions. The B side in FIG. 5, represents the oxidation reaction system of an oxidizable compound (e.g. an organic compound such as naphthalene) with ceric sulfate.

There was used an electrolytic cell 1 which comprised a platinum-electroplated titanium plate as an anode, a stainless steel (SUS 316L) plate as a cathode, a fluorinated resin-type cation exchange membrane as a diaphragm and a spacer.

In order to maintain the cerous sulfate concentration in the anolyte to be supplied to the anode side of the electrolytic cell 1 at a level of about 0.15 mol/liter, a cerous sulfate-ceric sulfate-aqueous sulfuric acid solution (hereinafter referred to simply as "an aqueous reaction solution") after the reaction in the reactor 3 in the reaction system at the B side in FIG. 5, was separated by a separator 4 and returned via a conduit 12 to the anolyte preparation tank 2, and an anolyte wherein the cerous sulfate concentration was maintained at about 0.15 mol/liter, was supplied from the preparation tank 2 via conduits 10 and 7 to the anode side of the electrolytic cell 1. On the other hand, from the electrolyte flowing out, after the electrolysis, from the electrolytic cell 1 via a conduit 8, an electrolyte corresponding to the amount of the aqueous reaction solution returned from the reaction system at the B side in FIG. 5, was withdrawn via a conduit 11 and supplied to the reaction system (i.e. the reactor 3), and the remaining electrolyte after the withdrawal (the majority of the electrolyte after the electrolysis) was returned to the above-mentioned preparation tank 2 via a conduit 9. On the other hand, from the catholyte tank 15, a 8% sulfuric acid aqueous solution was supplied as a catholyte via a conduit 16 to the cathode side of the elecrolytic cell 1 and used for the electrolysis, and then it was returned via a conduit 17 to the catholyte tank 15 and then recycled.

The electrolysis was conducted at an electrolytic temperature of 50° C., at a current density of 15 A/dm$^2$, at a voltage of about 3 V and at a flow rate in the electrolytic cell 1 of 40 cm/sec. The electrolyte flowing out, after the electrolysis, from the electrolytic cell 1 via a conduit 8 at a flow rate of 300 liter/hr at the A side in FIG. 5, had a composition wherein the cerous sulfate concentration was 0.15 mol/liter, the ceric sulfate concentration was 0.488 mol/liter and the sulfuric acid concentration was about 8.5%. (The changes in the amounts of the cerous sulfate and ceric sulfate in one pass through the electrolytic cell 1, were about $-6.25 \times 10^{-6}$ mol/liter and about $1.25 \times 10^{-5}$ mol/liter, respectively.) A part of this electrolyte i.e. 10 liter/hr, was withdrawn continuously via the conduit 11 and supplied to the reactor 3 in the reaction system at the B side in FIG. 5, as mentioned above. Into the reactor 3, an oxidizable compound (e.g. an organic compound such as naphthalene) was fed as a feed material via a supply pipe 5 and subjected to oxidation reaction. After the oxidation reaction, the reaction product was separated by a separator 4, withdrawn via a conduit 6 and supplied to a product process. The aqueous reaction solution separated from the reaction product in the separator 4 (composition: 0.194 mol/liter of cerous sulfate, 0.400 mol/liter of ceric sulfate and 10% of sulfuric acid), was returned via a conduit 12 to the preparation tank 2.

On the other hand, the major portion of the electrolyte withdrawn from the cell 1 was returned via the conduit 9 to the preparation tank 2, combined with the aqueous reaction solution returned via the conduit 12, and recycled to the electrolytic cell 1 via the conduits 10 and 7.

The current efficiency at that time was 98%.

We claim:

1. A method for electrolyzing cerous sulfate in the electrolytic oxidation of cerous sulfate to ceric sulfate in an aqueous sulfuric acid solution, characterized in that the concentration of the cerous sulfate in the electrolyte to be supplied to the electrolytic cell is maintained, by the presence of ceric sulfate, at a level of at least the saturated concentration of cerous sulfate in the aqueous sulfuric acid solution (exclusive of the cerous sulfate and ceric sulfate) at the initial sulfuric acid concentration and at the temperature of electrolysis, and at most the saturated concentration of cerous sulfate in the presence of the ceric sulfate in the aqueous sulfuric acid solution at the initial sulfuric acid concentration and at the temperature of electrolysis, and the concentration of the ceric sulfate in the electrolyte is maintained at a level of at most the saturated concentration of ceric sulfate in the aqueous sulfuric acid solution at the initial sulfuric acid concentration and at the temperature of electrolysis.

2. The method according to claim 1, wherein the concentration of sulfuric acid in the electrolyte is from about 5 to about 15% by weight.

3. The method according to claim 1, wherein the concentration of the cerous sulfate in the electrolyte at the outlet of the electrolytic cell is at least 0.08 mol/liter.

4. The method according to claim 1, wherein the temperature of electrolysis is from 30° to 80° C.

* * * * *